(12) United States Patent
Rice

(10) Patent No.: US 10,512,449 B2
(45) Date of Patent: Dec. 24, 2019

(54) INTRAVASCULAR DEVICE FOR VESSEL MEASUREMENT AND ASSOCIATED SYSTEMS, DEVICES, AND METHODS

(71) Applicant: Volcano Corporation, San Diego, CA (US)

(72) Inventor: Cheryl D. Rice, San Diego, CA (US)

(73) Assignee: VOLCANO CORPORATION, San Diego, CA (US)

( * ) Notice: Subject to any disclaimer, the term of this patent is extended or adjusted under 35 U.S.C. 154(b) by 674 days.

(21) Appl. No.: 14/857,368

(22) Filed: Sep. 17, 2015

(65) Prior Publication Data
US 2016/0081657 A1    Mar. 24, 2016

Related U.S. Application Data

(60) Provisional application No. 62/052,896, filed on Sep. 19, 2014.

(51) Int. Cl.
| A61B 8/00 | (2006.01) |
| A61B 8/12 | (2006.01) |
| A61B 8/08 | (2006.01) |

(52) U.S. Cl.
CPC .............. *A61B 8/445* (2013.01); *A61B 8/12* (2013.01); *A61B 8/0891* (2013.01); *A61B 8/4488* (2013.01)

(58) Field of Classification Search
CPC ......... A61B 8/445; A61B 8/12; A61B 8/4488; A61B 8/0891; A61B 5/02007; A61B 5/026; A61B 5/0215
See application file for complete search history.

(56) References Cited

U.S. PATENT DOCUMENTS

| 5,105,818 A * | 4/1992 | Christian ................ A61B 8/06 600/463 |
| 5,611,343 A * | 3/1997 | Wilson ..................... A61B 8/14 128/916 |
| 5,846,205 A * | 12/1998 | Curley ................ A61B 1/0052 600/472 |
| 5,857,974 A * | 1/1999 | Eberle .................. A61B 1/0011 29/25.35 |
| 6,110,121 A * | 8/2000 | Lenker .................... A61B 8/12 600/463 |
| 6,641,540 B2 | 11/2003 | Fleischman et al. |

(Continued)

*Primary Examiner* — Bo Joseph Peng

(57) ABSTRACT

An intravascular ultrasound (IVUS) device includes a catheter body having a proximal portion and an opposing distal portion; a transducer array disposed adjacent the distal portion, the transducer array having a plurality of transducers and each of the plurality of transducers having a maximum width, wherein the plurality of transducers are positioned circumferentially around the catheter body with a minimum spacing between adjacent transducers that is at least twice as large as the maximum width. A minimally invasive measuring device includes an elongate body configured for insertion in a patient, the elongate body having a proximal portion and an opposing distal portion; and a transducer array disposed adjacent the distal end, the transducer array having a plurality of transducers disposed circumferentially around the elongate body, the plurality of transducers comprising 3 to 16 transducers. A method of generating an intravascular measurement using an intravascular device is provided.

18 Claims, 9 Drawing Sheets

(56) References Cited

U.S. PATENT DOCUMENTS

| | | |
|---|---|---|
| 6,776,763 B2 | 8/2004 | Nix et al. |
| 7,226,417 B1 | 6/2007 | Eberle |
| 7,846,101 B2 | 12/2010 | Eberle et al. |
| 2008/0039742 A1* | 2/2008 | Hashimshony ...... A61B 5/0071 600/587 |
| 2011/0112400 A1* | 5/2011 | Emery ................ A61B 8/12 600/439 |
| 2012/0310064 A1* | 12/2012 | McGee ............... A61B 8/0883 600/373 |
| 2014/0187960 A1 | 7/2014 | Corl |

* cited by examiner

INTRAVASCULAR DEVICE FOR VESSEL MEASUREMENT AND ASSOCIATED SYSTEMS, DEVICES, AND METHODS

CROSS REFERENCE TO RELATED APPLICATIONS

The present application claims priority to and the benefit of the U.S. Provisional Patent Application No. 62/052,896, filed Sep. 19, 2014, which is hereby incorporated by reference in its entirety.

TECHNICAL FIELD

The present disclosure relates generally to systems, devices, and methods employing an intravascular device for diagnostically assessing a target region of a patient. More particularly, the present disclosure relates to systems, devices, and methods that utilize intravascular ultrasound (IVUS) devices for generating measurements, for example, within a patient's vasculature with relatively fewer transducers compared to IVUS devices for intravascular imaging.

BACKGROUND

Intravascular ultrasound (IVUS) imaging is widely used in interventional cardiology as a diagnostic tool for assessing a diseased vessel, such as an artery, within the human body to determine the need for treatment, to guide the intervention, and/or to assess its effectiveness. IVUS imaging uses ultrasound echoes to form a cross-sectional image of the vessel of interest. Typically, the ultrasound transducer on an IVUS catheter both emits ultrasound pulses and receives the reflected ultrasound echoes. The ultrasound waves pass easily through most tissues and blood, but they are partially reflected by discontinuities arising from tissue structures (such as the various layers of the vessel wall), red blood cells, and other features of interest. The IVUS imaging system, which is connected to the IVUS catheter by way of a patient interface module, processes the received ultrasound echoes to produce a cross-sectional image of the vessel where the catheter is located.

There are two types of IVUS catheters in common use today: solid-state and rotational, with each having advantages and disadvantages. Solid-state IVUS catheters use an array of ultrasound transducers (typically 64) distributed around the circumference of the catheter and connected to an electronic multiplexer circuit. The multiplexer circuit selects array elements for transmitting an ultrasound pulse and receiving the echo signal. By stepping through a sequence of transmit-receive pairs, the solid-state IVUS system can synthesize the effect of a mechanically scanned transducer element, but without moving parts. Since there is no rotating mechanical element, the transducer array can be placed in direct contact with the blood and vessel tissue with minimal risk of vessel trauma and the solid-state scanner can be wired directly to the imaging system with a simple electrical cable and a standard detachable electrical connector.

In the typical rotational IVUS catheter, a single ultrasound transducer element fabricated from a piezoelectric ceramic material is located at the tip of a flexible driveshaft that spins inside a plastic sheath inserted into the vessel of interest. The transducer element is oriented such that the ultrasound beam propagates generally perpendicular to the axis of the catheter. The fluid-filled sheath protects the vessel tissue from the spinning transducer and driveshaft while permitting ultrasound signals to propagate from the transducer into the tissue and back. As the driveshaft rotates (typically at 30 revolutions per second), the transducer is periodically excited with a voltage pulse to emit a short burst of ultrasound. The same transducer then listens for the returning echoes reflected from various tissue structures, and the IVUS imaging system assembles a two dimensional display of the vessel cross-section from a sequence of several hundred of these ultrasound pulse/echo acquisition sequences occurring during a single revolution of the transducer.

Manufacturers typically focus on maximizing the fidelity of the images generated by an IVUS imaging device. Thus, these devices generally include a large number of elements to optimize image quality and consistency so that detailed images of vessel morphology are generated. As a result, manufacturing the imaging device can be complex. For example, solid-state imaging devices, such as those illustrated in FIGS. 2 and 3, can be configured with numerous transducers and associated transducer control circuits. For example, an imaging device 200 can include eight or more transducer control circuits 202 that are used to control sixty-four or more transducers 204. Manufacturing can be inefficient and expensive because of the complexity of the devices. The large number of elements also increases the size of solid-state imaging devices. This can have adverse effects on maneuverability of the device within a patient's vasculature. Further, in some instances, diagnostic procedures do not necessarily require a high resolution image of vessel morphology. Rather, only clinically acceptable lumen measurements may be needed. Currently, however, such measurements can be determined only by analyzing a detailed image generated using a complex, expensive, and large IVUS device.

Accordingly, there remains a need for improved devices, systems, and methods for providing a compact intravascular device for generating vessel measurements that can be manufactured in an efficient manner.

The present disclosure addresses one or more of the shortcomings in the prior art.

SUMMARY

Embodiments of the present disclosure provide an intravascular ultrasound (IVUS) device for generating vessel measurements. The intravascular device has an ultrasound transducer array with relatively fewer transducers than other IVUS devices that are used primarily for intravascular imaging. The IVUS device also has relatively fewer components, such as one control circuit for the transducer array. The IVUS device is smaller and less complex, and as a result, manufacturing the IVUS device is more efficient and cost-effective.

In an exemplary aspect, the present disclosure is directed to an intravascular ultrasound (IVUS) device. The device includes a catheter body having a proximal portion and an opposing distal portion; and a transducer array disposed adjacent the distal portion, the transducer array having a plurality of transducers and each of the plurality of transducers having a maximum width, wherein the plurality of transducers are positioned circumferentially around the catheter body with a minimum spacing between adjacent transducers that is at least twice as large as the maximum width.

In some aspects, the transducer array has less than 24 transducers. In some aspects, the transducer array has less than 12 transducers. In some aspects, the transducer array has 6 transducers. In some aspects, the minimum spacing is greater than 4 times the maximum width. In some aspects, the minimum spacing is greater than 8 times the maximum width. In some aspects, the transducer array is connected to a control circuit, the control circuit having a width substantially greater than the maximum width and substantially equal to or greater than the minimum spacing. In some aspects, at least one of the transducer array and the control circuit comprise a flexible substrate. In some aspects, the device further includes a pressure sensor disposed adjacent the transducer array. In some aspects, the device further includes a control circuit receiving signals from both the transducer array and the pressure sensor.

In an exemplary aspect, the present disclosure is directed to a minimally invasive measuring device. The device includes an elongate body configured for insertion in a patient, the elongate body having a proximal portion and an opposing distal portion; and a transducer array disposed adjacent the distal end, the transducer array having a plurality of transducers disposed circumferentially around the elongate body, the plurality of transducers comprising 3 to 16 transducers.

In some aspects, the transducers are equally spaced about the circumference of the catheter body. In some aspects, the device further includes a single control circuit disposed adjacent the distal portion for controlling the transducer array. In some aspects, the device further includes a pressure sensor disposed adjacent the distal portion and in communication with the single control circuit. In some aspects, the transducer array is positioned more distally than the pressure sensor. In some aspects, the distal portion includes a guidewire-through lumen extending through the transducer array that terminates prior to reaching the proximal portion.

In an exemplary aspect, the present disclosure is directed to a method of generating an intravascular measurement. The method includes positioning an intravascular device within a vessel, the intravascular device comprising: a catheter body having a proximal portion and an opposing distal portion; and a transducer array disposed adjacent the distal portion, the transducer array having a plurality of transducers and each of the plurality of transducers having a maximum width, wherein the plurality of transducers are positioned circumferentially around the catheter body with a minimum spacing between adjacent transducers that is at least twice as large as the maximum width; controlling the transducer array to transmit ultrasonic energy and receive ultrasound echoes; processing, with a computing device in communication with the intravascular device, the ultrasound echoes to generate the intravascular measurement; and outputting the intravascular measurement to a display in communication with the computing device.

In some aspects, the transducer array is oriented at a first angular relation with respect to the vessel. In some aspects, the method further includes reorienting the intravascular device such that the transducer array is oriented about a longitudinal axis of the vessel at a second angular relation with respect to the vessel; and controlling the transducer array to transmit ultrasonic energy and receive ultrasound echoes while the transducer array is oriented at the second angular relation with respect to the vessel. In some aspects, the method further includes processing the ultrasound echoes associated with first and second angular relations to generate an average intravascular measurement. In some aspects, the second angular relation is different than the first angular relation. In some aspects, the method further includes monitoring the orientation of the transducer array. In some aspects, the intravascular measurement comprises at least one of a cross-sectional area and a diameter of a lumen of the vessel. In some aspects, the method further includes measuring a pressure of blood flow at a first location within the vessel using a pressure sensor disposed adjacent the distal portion of the catheter body; and outputting the pressure to the display. In some aspects, the method further includes measuring the pressure of blood flow at a second location within the vessel using the pressure sensor, wherein the first and second locations are respectively distal to and proximal to a stenosis in the vessel; computing a fractional flow reserve (FFR) using the pressure measurements at the first and second locations; and outputting the FFR to the display.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

Figure 1:
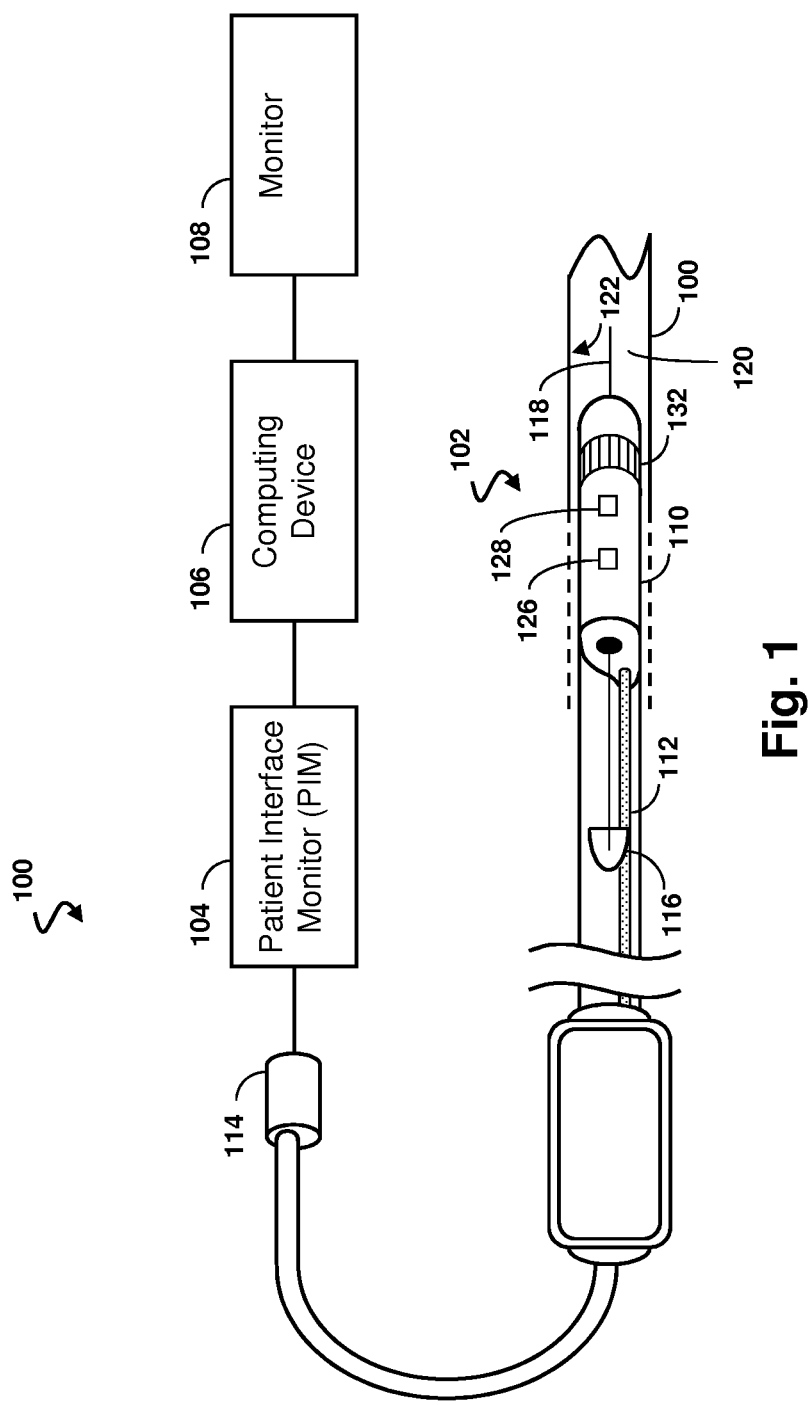
FIG. 1 is a diagrammatic schematic view of an imaging system, according to an embodiment of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

Embodiments of the present disclosure provide an elongated intravascular device, such as a solid-state catheter, with a transducer array having a reduced quantity of transducer elements. The total quantity of components in the intravascular device is also less than IVUS imaging devices designed for intravascular imaging. For example, the transducer array can be controlled using one integrated transducer control circuit. By minimizing the quantity of transducer elements and other components, the size or profile of the intravascular device can also be minimized or otherwise optimized for traversing a patient's vasculature. The reduced complexity intravascular device is simpler to assemble, resulting in an easier, more efficient, and more cost-effective manufacturing process.

Rather than generating a high fidelity intravascular image, embodiments of the present disclosure focus primarily on collecting sufficient IVUS data to generate clinically acceptable vessel measurements. For example, the diameter and/or cross-sectional area of a lumen of a blood vessel can be roughly determined from the collected IVUS data. The vessel measurements can be utilized during pre-treatment/diagnostic procedures to guide treatment choices. For example, the vessel measurements can be used to identify areas of plaque buildup or other narrowing of the vessel. For example, the vessel measurements generated by the intravascular device can guide the choice of a stent diameter and/or length. The vessel measurements can also be utilized during post-treatment procedures to assess treatment. For example, the vessel measurements generated by the intravascular device can be used to determine the efficacy of stenting.

While the intravascular devices of the present disclosure do not generate detailed images of vessel morphology, the IVUS data can be used to generate images in which high-density objects such as calcium and stent struts are identifiable. For example, during a pre-treatment procedure, the IVUS device can generate an image in which significant areas of calcification, which can hamper treatment, are visible. During a post-treatment procedure, the IVUS device can generate in image in which stent apposition can be assessed based on the position of the stent struts.

Referring to FIG. 1, shown therein is an imaging system 100 according to an embodiment of the present disclosure. The imaging system 100 includes an elongated intravascular device 102 such as a catheter, guidewire, or guide catheter, a patient interface module (PIM) 104, a computing device 106, and a monitor 108. The imaging system 100 can be used to measure the diameter and/or the cross-sectional area of a lumen in a target region of interest. In that regard, the intravascular device 102 can be positioned within the target region of interest, such as within the vasculature of a human body. For example, the intravascular device 102 can be positioned within a vessel 100 and configured to measure the diameter and/or the cross-sectional area of a lumen 120 of the vessel 100. The lumen 120, with a lumen wall 122, extends along the length of the vessel 100. In that regard, the lumen 120 allows flow of fluid through the vessel. In some instances, the vessel 100 is a blood vessel. In some particular instances, the vessel 100 is a coronary artery. In such instances, the lumen 120 is configured to facilitate the flow of blood through the vessel 100.

At a high level, the intravascular device 102 can be a solid-state IVUS device. In that regard, the intravascular device 102 can emit ultrasonic energy from transducer elements included in a scanner assembly 110 mounted at or near a distal end of the IVUS device 102. The solid-state IVUS device 102 includes an array of transducer elements 132. The array of transducer elements 132 can be positioned in an annular configuration about a longitudinal axis of the IVUS device 102. The emitted ultrasonic energy is reflected by tissue structures in the medium surrounding the scanner assembly 110, and the ultrasound echo signals are received by the transducer elements. The transducer array 132 can be positioned at or adjacent a distal portion of the intravascular device 102 in some instances. In that regard, the transducer elements can be positioned less than 30 cm, less than 10 cm, less than 5 cm, less than 3 cm, less than 2 cm, and/or less than 1 cm from a distal tip of the IVUS device 102 in some instances. It is understood that the transducer elements can be positioned at any position along the intravascular device 102, including any distance from the distal tip. In some instances, the transducer array 132 can be positioned at the distal tip of the IVUS device 102.

The intravascular device 102 can include one or more sensing element(s) 128 at or adjacent the distal portion of the intravascular device 102. It is understood that the sensing element 128 can be positioned at any position along the intravascular device 102, including any distance from the distal tip. For example, the transducer array 132 can be positioned more distally or more proximally than the sensing element 128. In some embodiments, the sensing element 128 is a pressure transducer configured to detect data indicative of pressure within the blood vessel 100. While emitting ultrasonic energy and receiving echoes, or at intermittent intervals, the intravascular device 102 takes pressure readings within the target body region, often within the vasculature of a patient. In other embodiments, the sensing element 128 can be a flow sensor, a temperature sensor, a pressure sensor, and/or other suitable components.

The scanner assembly 110 includes integrated circuit controller chip(s) 126 configured to activate transmitter circuitry to generate an electrical pulse to excite the elements of the transducer array 132 and to accept echo signals received from the transducer elements and/or amplify the echo signals via amplifiers included thereon. The control circuit also acts as a multiplexer to combine multiple signals into a single wire to reduce the number of overall wires running down the device. In some embodiments, the scanner assembly 110 includes a plurality of controllers 126. In some embodiments, the intravascular device 102 includes one controller or control circuit 126. The controller 126 can be an application-specific integrated circuit (ASIC). The controller 126 can be configured to select the particular elements of transducer array 132 to be used for transmit and receive, to select the frequency of the transmit signal from the transducer element(s), and perform other functions as described herein or related to the functions described herein. The processing architecture of the controller chip 126 can be similar to the one described in U.S. Provisional Application No. 61/746,804, filed Dec. 28, 2012, now published as U.S. Patent Application Publication No. 2014/0187960 on Jul. 3, 2014, and/or U.S. Provisional Application No. 62/032,368, filed Aug. 1, 2014, the entireties of which are hereby incorporated by reference. The controller 126 can also be configured to receive signals from the sensing element 128, such as electrical signals representative of sensed pressure from a pressure transducer. In that regard, the transducer array 132 and the sensing element 128 can share the same controller and share the same communication and power cable 112 (also referred to herein as a transmission line bundle 112) extending toward the proximal end of the intravascular device 102.

In some embodiments, the IVUS device includes some features similar to traditional solid-state IVUS catheters, such as the EagleEye® catheter available from Volcano Corporation and those disclosed in U.S. Pat. No. 7,846,101 hereby incorporated by reference in its entirety. For example, the intravascular device 102 includes the scanner assembly 110 near a distal end of the device 102 and the transmission line bundle 112 extending along the longitudinal body of the device 102. The transmission line bundle 112 terminates in a PIM connector 114 at a proximal end of the device 302. The PIM connector 114 electrically couples the transmission line bundle 112 to the PIM 304 and physically couples the intravascular device 102 to the PIM 104. In an embodiment, the intravascular device 102 further includes a guidewire exit port 116. Accordingly, in some instances the IVUS device is a rapid-exchange catheter. The guidewire exit port 116 allows a guidewire 118 to be inserted towards the distal end in order to direct the device IVUS 102 through the vessel 100. In some embodiments, as described with respect to FIG. 6, the reduced transducer intravascular device can be implemented as a monorail catheter.

The imaging system 100 includes the PIM 104 that facilitates communication of signals between the computing device 106 and the intravascular device 102 to control the operation of the transducer array 132 and/or the sensing element 128. Controlling the operation of the transducer array 132 can include, among others, the steps of: (1) providing commands to the controller 126, (2) providing the transmit trigger signals to the controller 126 to activate the transmitter circuitry to generate an electrical pulse to excite transducer elements, and (3) accepting amplified echo signals received from the transducer elements via amplifiers included on the controller 126. In some embodiments, the PIM 104 performs preliminary processing of the echo data prior to relaying the data to the computing device 106. In examples of such embodiments, the PIM 104 performs amplification, filtering, and/or aggregating of the data. In an embodiment, the PIM 104 also supplies high- and low-voltage DC power to support operation of the intravascular device 102 including circuitry within the scanner assembly 110. The PIM 104 transfers the received echo signals to the computing device 106 where, among other things, measurements and/or ultrasound images of the vessel 100 can be reconstructed and displayed on the monitor 108. At the same time, the PIM 104 forwards sensing data received from the sensing element 128 (e.g., pressure data from the pressure transducer) and, in some embodiments, performs preliminary signal processing prior to transmitting the data to the computing device 106. In examples of such embodiments, the PIM 104 performs amplification, filtering, and/or aggregating of the sensing data. The PIM 104 also transfers the received data to the computing device 106 where, among other things, when the received data is pressure data, a fractional flow reserve (FFR) can be calculated based on the obtained pressure measurements.

The computing device 106 receives the echo data from the transducer array 132 and sensing data from the sensing element 128 (e.g., pressure data from the pressure transducer) by way of the PIM 104. The computing device 106 processes the echo data to generate one or more intravascular measurements, such as a cross-sectional area and/or a diameter of the lumen 120. The computing device 106 can also processes the echo data to create an IVUS image of the tissue surrounding the transducers and/or assesses the pressure within the target region. The IVUS image can be a B-scan image representative of the two-dimensional anatomical structure of the tissue in a plane perpendicular to the longitudinal axis of intravascular device 102, with brightness at any point of the image representing of the strength of the echo signal received from the corresponding location within the tissue. As noted herein, a detailed IVUS image with complete vessel morphology is not generated with the reduced quantity of transducers in the transducer array 132. However, the IVUS image generated according to embodiments of the present disclosure can visualize high density objects (such as calcification and/or stent struts) in the vessel 100, which appear as saturated portions in the IVUS image.

When the sensing element 128 includes a pressure transducer, the computing device 106 processes the pressure data to calculate a fractional flow reserve (FFR) based on the obtained pressure measurements. FFR is a currently accepted technique for assessing the severity of a stenosis in a blood vessel, including ischemia-causing lesions. It is defined as the ratio of the maximal blood flow in a stenotic artery, taken distal to the lesion, to normal maximal flow. Accordingly, to calculate the FFR for a given stenosis, two blood pressure measurements are taken: one measurement distal or downstream to the stenosis and one measurement proximal or upstream to the stenosis. FFR is a calculation of the ratio of the distal pressure measurement relative to the proximal pressure measurement. FFR provides an index of stenosis severity that allows determination as to whether the blockage limits blood flow within the vessel to an extent that treatment is required. The more restrictive the stenosis, the greater the pressure drop across the stenosis, and the lower the resulting FFR. FFR measurements can be used as a decision point for guiding treatment decisions. The normal value of FFR in a healthy vessel is 1.00, while values less than about 0.80 are generally deemed significant and require treatment. Common treatment options include angioplasty, atherectomy, and stenting. The computing device 106 can generate and provide display data to the monitor 108 to display the computed vessel measurement(s), the IVUS image, and/or pressure information, including the FFR. The monitor 108 is configured to display data collected by the intravascular device 102 and/or data generated by the computing device 110.

The computing device 106 can be generally representative of any device suitable for performing the processing and analysis techniques discussed within the present disclosure. In some embodiments, the computing device 106 includes a processor, random access memory, and a storage medium. In that regard, in some particular instances the computing device 106 is programmed to execute steps associated with the data acquisition and analysis described herein. Accordingly, it is understood that any steps related to data acquisition, data processing, instrument control, and/or other processing or control aspects of the present disclosure may be implemented by the computing device 106 using corresponding instructions stored on or in a non-transitory computer readable medium accessible by the computing device. In some instances, the computing device 106 is a console device. In some particular instances, the computing device 106 is similar to the s5™ System or the s5™ Imaging System, each available from Volcano Corporation. In some instances, the computing device 106 is portable (e.g., handheld, on a rolling cart, etc.). Further, it is understood that in some instances the computing device 106 comprises a plurality of computing devices. In that regard, it is particularly understood that the different processing and/or control aspects of the present disclosure may be implemented separately or within predefined groupings using a plurality of computing devices. Any divisions and/or combinations of the processing and/or control aspects described below across multiple computing devices are within the scope of the present disclosure.

Figure 2:
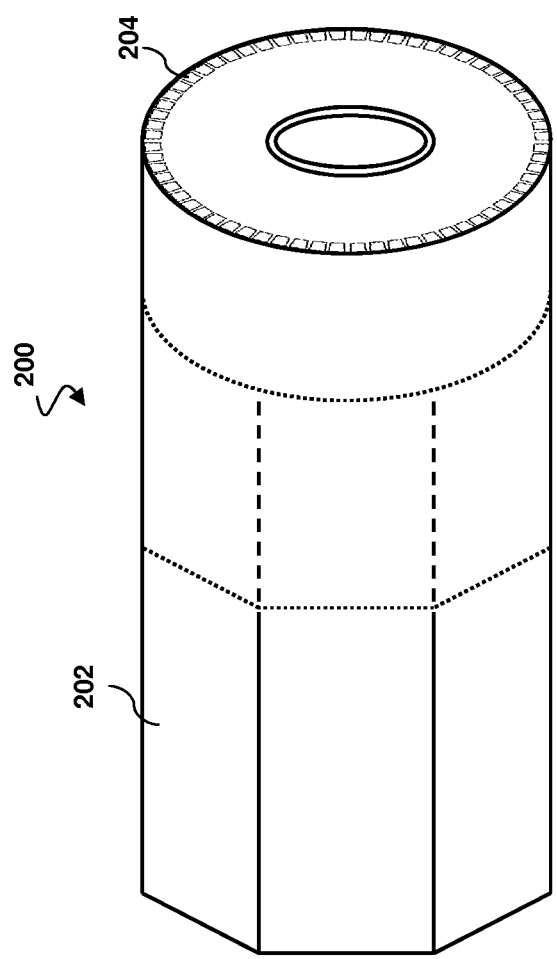
FIG. 2 is a diagrammatic, partial cutaway perspective view of an imaging device.
Figure 3:
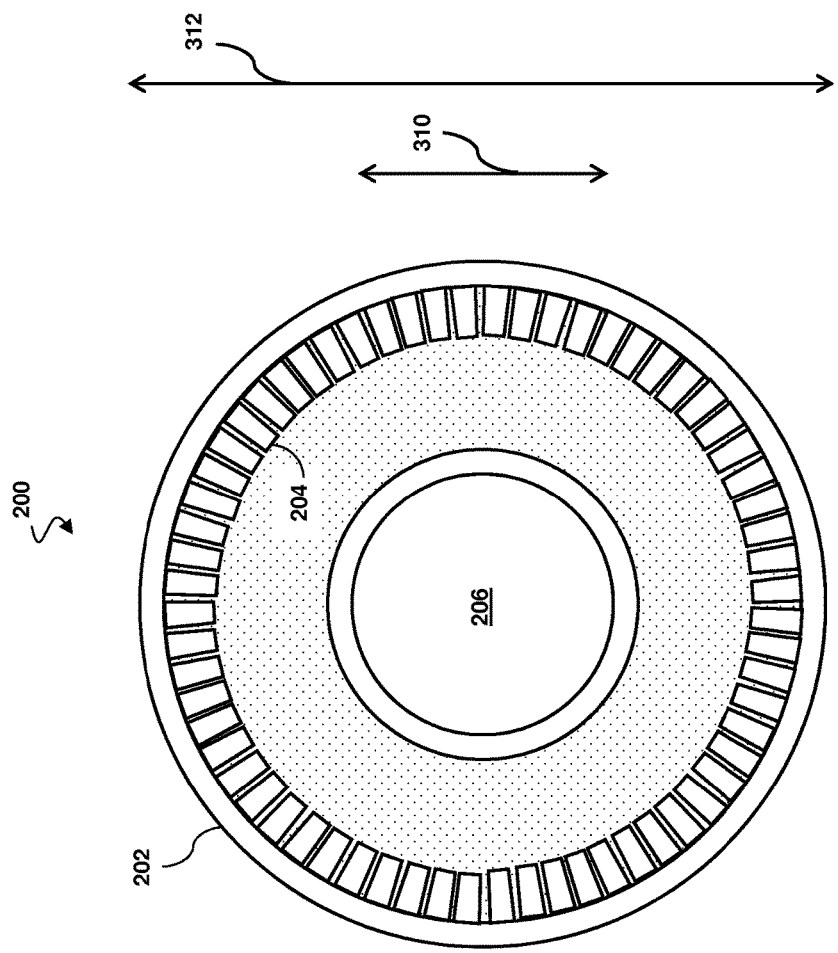
FIG. 3 is a diagrammatic, cross-sectional end view of a distal portion of the imaging device of FIG. 2.

FIGS. 2 and 3 illustrate imaging devices that are configured to generate high resolution IVUS images. FIG. 2 is a diagrammatic, partial cutaway perspective view of the imaging device, and FIG. 3 is a diagrammatic, cross-sectional end view of a distal portion of the imaging device of FIG. 2. The imaging device 200 includes multiple controllers 202 that are configured to control multiple transducer elements 204. For example, the imaging device 200 can include eight or more controllers 202 and sixty-four or more transducer elements 204. The imaging device 200 includes a lumen region 206 that is open to allow the imaging device 200 to be advanced over a guidewire. The lumen region has a diameter 310. The imaging device 200 has an outer diameter 312.

Figure 4:
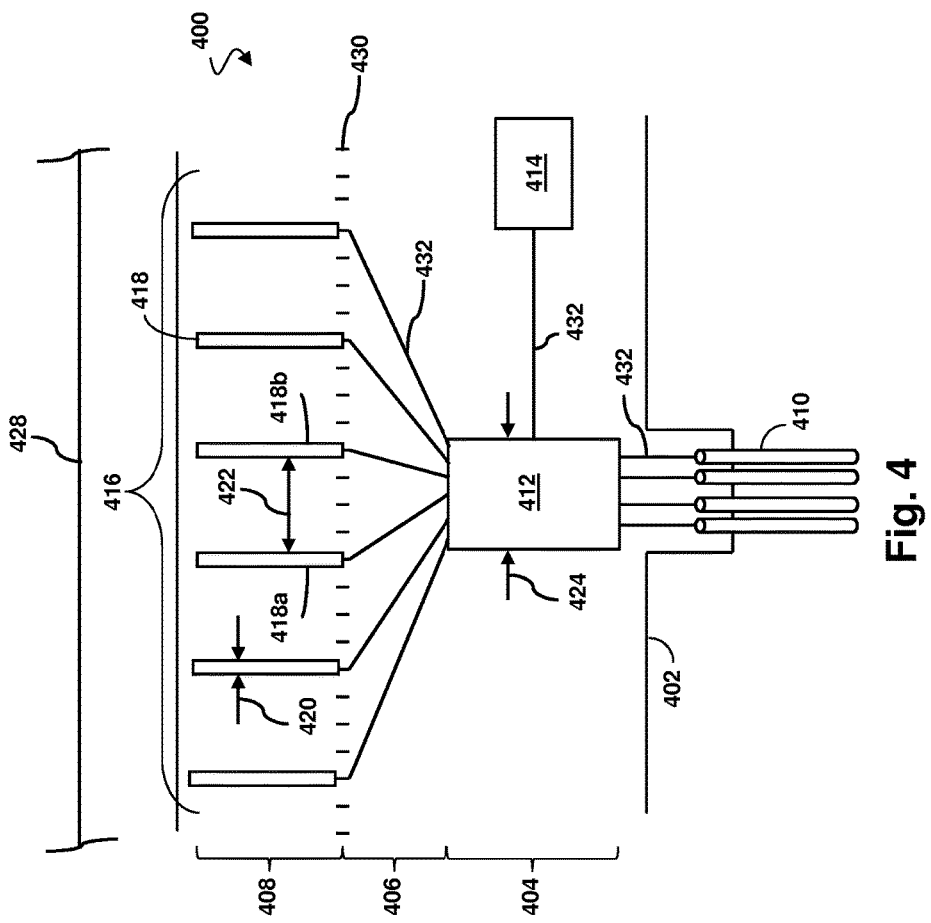
FIG. 4 is a diagrammatic top view of a distal portion of a reduced transducer intravascular device, according to an embodiment of the present disclosure, with the distal portion being arranged in a flat configuration.

FIG. 4 illustrates a diagrammatic top view of a scanner assembly 400 of a reduced transducer intravascular device, according to an embodiment of the present disclosure. The scanner assembly 400 can be implemented at a distal portion of the intravascular device 102 (FIG. 1). In that regard, the scanner assembly 400 can be similar to the scanner assembly 110. The scanner assembly 400 can be associated with the patient interface module (PIM) 104, the computing device 106, and/or the monitor 108 (FIG. 1). The scanner assembly 400 is shown in a flat configuration in FIG. 4. When disposed on the intravascular device 102, the scanner assembly 400 is rolled into a cylindrical form (as shown in, e.g., FIGS. 1 and 5). The assembly 400 includes a measurement transducer array 416 and a transducer control circuit 412, attached to a flexible circuit or flexible substrate 402. The transducer array 416 and the transducer control circuit 412 can be similar to the transducer array 132 (FIG. 1) and the transducer control circuit 126 (FIG. 1), respectively. In some embodiments, scanner assembly 400 can include a sensing element 414, such as a pressure sensor. The sensing element 414 can be similar to the sensing element 128 (FIG. 1). The scanner assembly 400 includes a transducer region 408, a control region 404, and a transition region 406 extending between the transducer region 408 and the control region 404. The length of the regions 404, 406, 408 can vary in different embodiments, depending on, e.g., the size and/or position of the control circuit 412, transducer array 416, and other components of the scanner assembly 400.

The measurement transducer array 416 includes a plurality of ultrasound transducers 418. In a cylindrical or rolled configuration (as shown in, e.g., FIG. 5), the plurality of ultrasound transducers 418 are disposed circumferentially around the body of the intravascular device. In some embodiments, the transducers are equally spaced about the circumference of the body of the intravascular device. The transducer array 416 may include any number and type of ultrasound transducers 418, although for clarity only a limited number of ultrasound transducers are illustrated in FIG. 4. In some embodiments, the transducer array 416 includes less than 64 transducers, less than 32 transducers, less than 24 transducers, less than 16 transducers, less than 12 transducers, etc. In some embodiments, the transducer array 416 includes between 3 and 24 transducers, between 3 and 16 transducers, between 3 and 12 transducers, etc., including values such as 3 transducers, 6 transducers, 8 transducers, 9 transducers, 12 transducers, 15 transducers, 16 transducers, 18 transducers, 20 transducers, 21 transducers, 24 transducers, etc. Other quantities of transducers are both contemplated and provided for. As described herein, the transducer array 416 includes relatively fewer ultrasound transducers 418 compared to IVUS devices for intravascular imaging (e.g., the imaging device 200 of FIGS. 2 and 3). To illustrate the comparison to IVUS devices for intravascular imaging, the locations on the flex circuit 402 where the additional transducer elements could be positioned are indicated by the hash marks 430. (FIG. 5 also includes the additional transducer elements 430, which are shown in phantom lines.) As shown in FIG. 4, transducer elements are not positioned on the hash marks 430 in embodiments of the present disclosure.

In an embodiment, the ultrasound transducers 418 of the measurement transducer array 416 are piezoelectric micromachined ultrasound transducers (PMUTs) fabricated on a microelectromechanical system (MEMS) substrate using a polymer piezoelectric material, for example as disclosed in U.S. Pat. No. 6,641,540, which is hereby incorporated by reference in its entirety. In alternate embodiments, the transducer array includes piezoelectric zirconate transducers (PZT) transducers such as bulk PZT transducers, capacitive micromachined ultrasound transducers (cMUTs), single crystal piezoelectric materials, other suitable ultrasound transmitters and receivers, and/or combinations thereof.

In the illustrated embodiment, the scanner assembly 400 includes one transducer control circuit or controller 412. The control circuit 412 controls the transducer array 416, and is disposed at or adjacent the distal portion of the intravascular device. The single controller 412 can receive signals directly from the communication and power cable 410. The cable 410 can be similar to the transmission line bundle 112 (FIG. 1). The controller 412 can generate electrical pulse(s) to excite one or more transducer elements 418 to transmit ultrasonic energy and/or accept echo signal received from the transducer elements. The controller 412 can retransmit the echo data to, e.g., the PIM 104 (FIG. 1) via the cable 410. In some embodiments, the controller 412 includes an echo amplifier. In this configuration, the controller 412 receives unamplified or partially amplified echo data and performs the necessary amplification for driving the echo data along conductors of the cable 410. The controller 412 drives each of the transducer elements 418. For example, the transducer array 416 can include eight transducers 418, all of which are assigned to the single controller 412. In such embodiments, the controller 412 can be referred to as an 8-channel controller, based on the number of transducers 418 the controller is capable of driving. Designs incorporating more than one transducer control circuit 412 can be utilized in other embodiments. Various tasks can be carried out by the different controllers (e.g., a master controller and one or more slave controllers), as described in U.S. patent application Ser. No. 14/137,269, filed Dec. 20, 2013 now published as U.S. Patent Application Publication No. 2014/0187960 on Jul. 3, 2014, and/or U.S. Provisional Application No. 62/032,368, filed Aug. 1, 2014, both of which are incorporated herein by reference.

Figure 5:
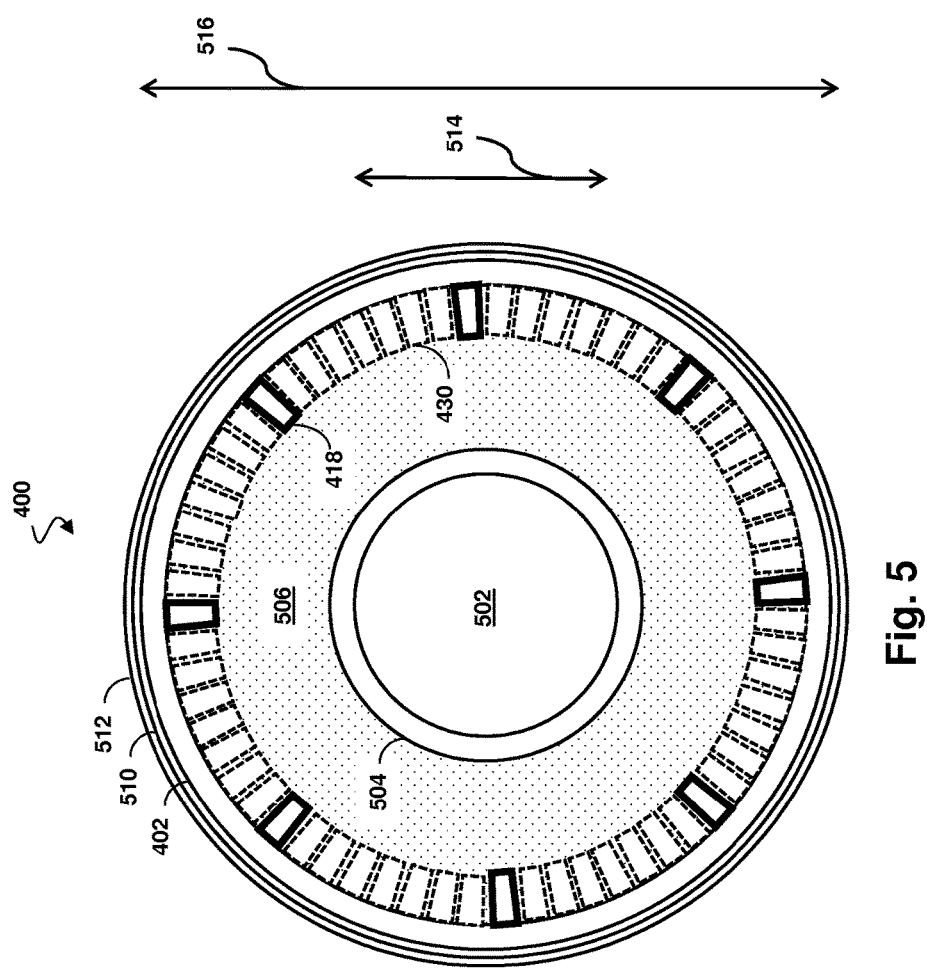
FIG. 5 is a diagrammatic, cross-sectional end view of the reduced transducer intravascular device of FIG. 4, including a comparison between the devices of FIGS. 3 and 4.

Each of the transducers 418 has a maximum width 420. The maximum width 420 can vary in different embodiments. For example, while FIG. 5 illustrates that each transducer 418 has the same width as the transducers 204 of the imaging device 200 (FIG. 3), in different embodiments, the maximum width 420 of the transducers 418 can be larger or smaller than the transducers 204. Adjacent transducers 418a, 418b can be separated by a minimum spacing 422. In various embodiments, the minimum spacing 422 is at least twice, at least four times, at least eight times, etc., as large as the maximum width 420. For example, the minimum spacing 422 can be two, three, four, six, eight, or more times as large as the maximum width 420. The control circuit 412 has a width 424. In some embodiments, the width 424 of the control circuit 412 is substantially greater than the maximum width 420 of the transducers 418. In some embodiments, the width 424 of the control circuit 412 is substantially equal to or greater than the minimum spacing 422 between adjacent transducers 418a, 418b. In some embodiments, the width 424 of the control circuit 412 is substantially less than a width of transducer array 416 and/or a width of the flex circuit 402.

The controller 412 and the transducers 418 are mounted on a flex circuit 402 that provides structural support and interconnects for electrical coupling. The flex circuit 402 may be constructed to include a film layer of a flexible polyimide material such as KAPTON™ (trademark of DuPont). Other suitable materials include polyester films, polyimide films, polyethylene napthalate films, or polyetherimide films, other flexible printed semiconductor substrates as well as products such as Upilex® (registered trademark of Ube Industries) and TEFLON® (registered trademark of E.I. du Pont). The film layer is configured to be wrapped around a ferrule to form a cylindrical toroid in some instances. Therefore, the thickness of the film layer is generally related to the degree of curvature in the final assembled scanner assembly 400. In some embodiments, the film layer is between 5 µm and 100 µm, with some particular embodiments being between 12.7 µm and 25.1 µm.

In an embodiment, the flex circuit 402 further includes conductive traces 432 formed on the film layer. Conductive traces 432 carry signals between the transducer control circuit 412 and the transducers 418 and provide a set of pads for connecting the conductors of electrical cable 410. Suitable materials for the conductive traces 432 include copper, gold, aluminum, silver, tantalum, nickel, and tin and may be deposited on the flex circuit 402 by processes such as sputtering, plating, and etching. In an embodiment, the flex circuit 402 includes a chromium adhesion layer. The width and thickness of the conductive traces 432 are selected to provide proper conductivity and resilience when the flex circuit 402 is rolled. A suitable width or thickness of a conductive trace 432 can be selected, for example, depending on the size of a pad of a device or the width of a wire to be coupled to the trace. Additional details of the flex circuit 402 may be found in U.S. patent application Ser. No. 14/137,269, filed Dec. 20, 2013 now published as U.S. Patent Application Publication No. 2014/0187960 on Jul. 3, 2014, and/or U.S. Provisional Application No. 62/032,368, filed Aug. 1, 2014, both of which are incorporated herein by reference.

In embodiments in which the scanner assembly 400 includes a sensing element 414, such as a pressure sensor, the sensing element 414 can disposed at various locations on the flexible circuit 402. For example, the sensing element 414 can be disposed at or beyond the top edge of the flex circuit 402 so as to not interfere with operation of the IVUS transducers 418. The sensing element 414 is under control of the controller 412. Conductive traces 432, similar to other conductive traces described herein, extend from the controller 412 to the sensing element 414. Data or information obtained by the sensing element 414 may be communicated to the control circuit 412, may receive some level of processing, amplification, or other treatment at the control circuit 412, and may then be communicated on the same electrical conductors of the cable 410 as the signals relating to information from the IVUS transducers 418. In one aspect, the control circuit 412 can digitize the one or more of the IVUS or pressure sensor signals prior to transmission.

FIG. 5 is a cross-sectional view of the transducer region 408 of the scanner assembly 400 (FIG. 4), according to an embodiment of the present disclosure. The transducer region 408 is depicted in its rolled form. In that regard, in some instances the scanner assembly 400 is transitioned from a flat configuration to a rolled or more cylindrical configuration. For example, in some embodiments, techniques are utilized as disclosed in one or more of U.S. Pat. No. 6,776,763, titled "ULTRASONIC TRANSDUCER ARRAY AND METHOD OF MANUFACTURING THE SAME" and U.S. Pat. No. 7,226,417, titled "HIGH RESOLUTION INTRAVASCULAR ULTRASOUND TRANSDUCER ASSEMBLY HAVING A FLEXIBLE SUBSTRATE," each of which is hereby incorporated by reference in its entirety.

The transducer region 408 of the scanner assembly 400 contains the transducers 418, which, as previously disclosed, are attached to the flex circuit 402, and in particular, to the traces of the flex circuit 402. For the sake of comparison, FIG. 5 illustrates in additional transducers 430 in phantom lines. The additional transducers 430 are included in IVUS devices for intravascular imaging (e.g., the imaging device 200 of FIGS. 2 and 3). As described herein, scanner assemblies of the present disclosure include relatively fewer transducers 418. Thus, the scanner assembly 400 omits the additional transducers 430. In the illustrated embodiment, the flex circuit 402 also includes a conductive ground layer 510. In a further embodiment, the flex circuit includes an outer membrane 512 used to insulate and cover the ground layer 510 and to protect the scanner assembly 400 from the environment. Insulator materials for the outer membrane 512 may be selected for their biocompatibility, durability, hydrophilic or hydrophobic properties, low-friction properties, ultrasonic permeability, and/or other suitable criteria. For example, the outer membrane may include Parylene™ (trademark of Union Carbide). Other suitable materials include heat shrink tubing such as polyester or PVDF, a melt-formable layers such as Pebax® (registered trademark of Arkema) or polyethylene, and/or other suitable membrane materials. In some instances, encapsulating epoxy 506 fills the spaces between the ultrasound transducers 418 and the ferrule 504. The lumen region 502 inside the ferrule 514 is open to allow the scanner assembly 400 and the intravascular device to be advanced over a guidewire. The lumen region 402 has a diameter 510. As can be seen, the size, shape, and spacing of the ultrasound transducers 418 at least partially define the shape of the transducer region 408. In various embodiments, a cross-section of the scanner assembly 400 is polygonal, circular, nearly circular, and/or a combination thereof.

The scanner assembly 400 has an outer diameter 516. In some embodiments, the outer diameter 516 of the scanner 400 can be the same as or similar to the outer diameter 312 of the imaging device 200 (FIG. 3). In some instances, a manufacturer or user may prefer that scanner assembly 400 maintain the same or similar outer diameter despite having relatively fewer transducer elements. For example, a manufacturer can more efficiently transition to manufacturing the scanner assembly 400 by changing only the number and position of transducers 418 while other dimensions of the scanner assembly 400 stay the same. For example, a physician may have greater familiarity maneuvering scanner assemblies of the same or similar diameter within a patient's vasculature. In some embodiments, the outer diameter 516 of scanner assembly 400 (FIG. 5) is less than the outer diameter 312 of the imaging device 200 (FIG. 3). For example, because the scanner assembly 400 includes relatively fewer transducers 418, the transducers 418 can be positioned with less space separating adjacent transducers, resulting in a smaller outer diameter 516. For similar reasons, in some embodiments, the diameter 514 of the lumen region 502 can be the same or similar to the diameter 310 of lumen region 206 (FIG. 3). Likewise, in some embodiments, the diameter 514 of the lumen region 502 can be smaller than the diameter 310. For example, the intravascular device can be advanced over a smaller diameter guidewire. A reduced diameter 514 of the lumen region 502 and/or a reduced outer diameter 516 can improve the maneuverability of the intravascular device within tortuous vessels of the patient's vasculature. In some embodiments, the inner diameter 514 of the lumen region 502 is sized to accommodate guidewires having diameters between about 0.014 and about 0.035 inches, and/or other suitable values. In some embodiments, the outer diameter 516 is between about 0.5 mm and about 3.0 mm and/or other suitable values. In further embodiments, the elongated intravascular device is a guidewire and the transducer array is mounted on the guidewire. In these embodiments, the guidewire and transducer array may have traditional diameters such as 0.014, 0.018 and 0.035 inches, or any diameters in-between.

Figure 6:
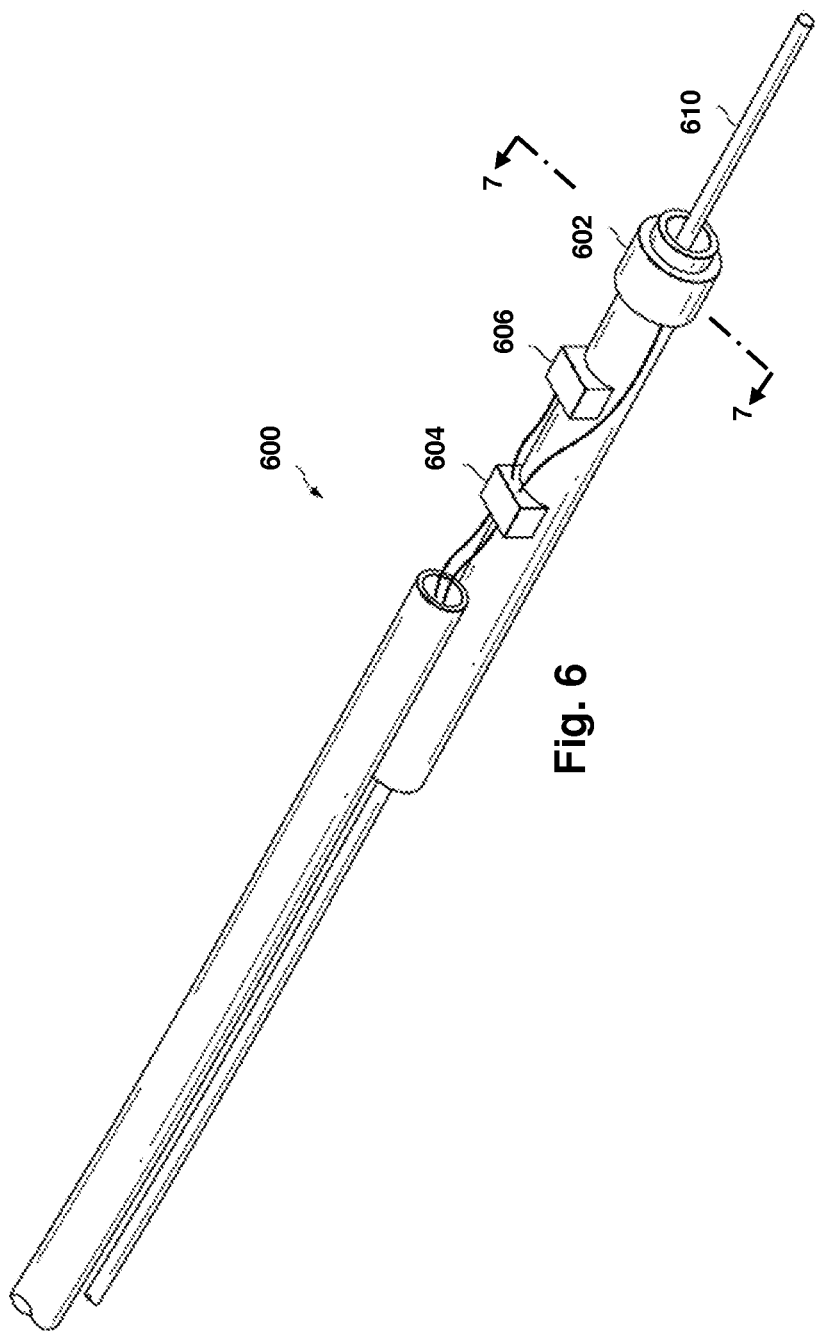
FIG. 6 is a perspective side view of a reduced transducer intravascular device, according to another embodiment of the present disclosure.

FIG. 6 illustrates a perspective side view of a reduced transducer intravascular device, according to another embodiment of the present disclosure. The intravascular device shown in FIG. 6 is a monorail pressure sensing catheter 600. A controller 604, a transducer array 602, and sensing element(s) 606 are disposed on or about the catheter 600. The controller 604 can be similar to the controller 126 (FIG. 1) and/or the controller 412 (FIG. 4). The transducer array 602 can be similar to the transducer array 132 (FIG. 1), the scanner assembly 110 (FIG. 1), the transducer array 416 (FIG. 4), and/or the scanner assembly 400 (FIG. 4). The sensing element 606 can be similar to the sensing element 128 (FIG. 1) and/or the sensing element 414 (FIG. 1). During use, the catheter 600 is advanced to a target region, e.g., within a patient's vasculature, over a guidewire 610.

Figure 7:
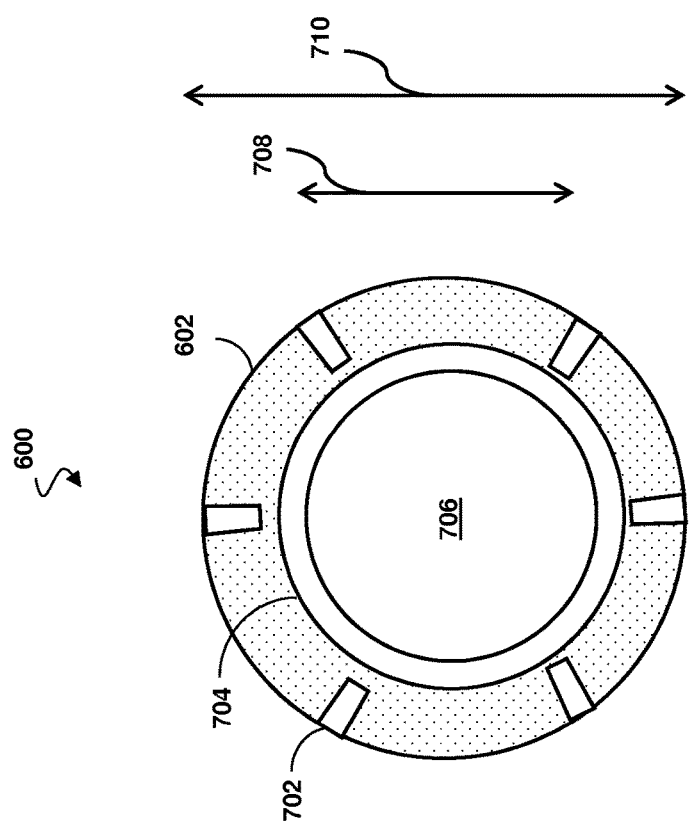
FIG. 7 is a diagrammatic, cross-sectional end view of the reduced transducer intravascular device of FIG. 6.

FIG. 7 illustrates a diagrammatic, cross-sectional end view of the catheter 600 (FIG. 6). The cross-sectional end view of FIG. 7 is taken along line 7-7 in FIG. 6. The transducer array 602 includes a plurality of transducer elements 702. The catheter 600 includes relatively fewer transducer elements 702 than IVUS devices for intravascular imaging (e.g., imaging device 200 of FIGS. 2 and 3). While the illustrated embodiment includes six transducers 702, it is understood that the catheter 600 can include other quantities of transducers, such as described with respect to the scanner assembly 400 of FIG. 4. For example, the catheter 600 can include between three and twelve transducers 702 in some embodiments. The plurality of ultrasound transducers 702 can be disposed circumferentially around the body of the intravascular device. In some embodiments, the transducers are equally spaced about the circumference of the body of the intravascular device. The lumen region 706 inside a ferrule 704 is open to allow transducer array 602 and the catheter 600 to be advanced over a guidewire. The lumen region 706 has a diameter 708. The transducer array 602 has an outer diameter 710. In some embodiments, the outer diameter 710 of the transducer array 602 (FIG. 7) is smaller than the outer diameter 312 of the imaging device 200 (FIG. 3). For example, because the transducer array 602 includes relatively fewer transducers 702, the transducers 702 can be positioned with less space separating adjacent transducers, resulting in a smaller outer diameter 710. Likewise, in some embodiments, the diameter 708 of the lumen region 706 can be smaller than the diameter 310 of the lumen region 206 (FIG. 3). For example, the catheter 600 can be advanced over a smaller diameter guidewire 610. A reduced diameter 708 of the lumen region 706 and/or a reduced outer diameter 710 can improve the maneuverability of the catheter 600 within tortuous vessels in the patient's vasculature. In some embodiments, the diameter 708 of the lumen region 706 is sized to accommodate guidewires having diameters between about 0.014 and about 0.035 inches, and/or other suitable values. In some embodiments, the outer diameter 710 is between about 0.5 mm and about 3.0 mm, and/or other suitable values. In some embodiments, the diameter 708 of the lumen region 706 can be the same or similar to the diameter 310 of lumen region 206 (FIG. 3).

Figure 8:
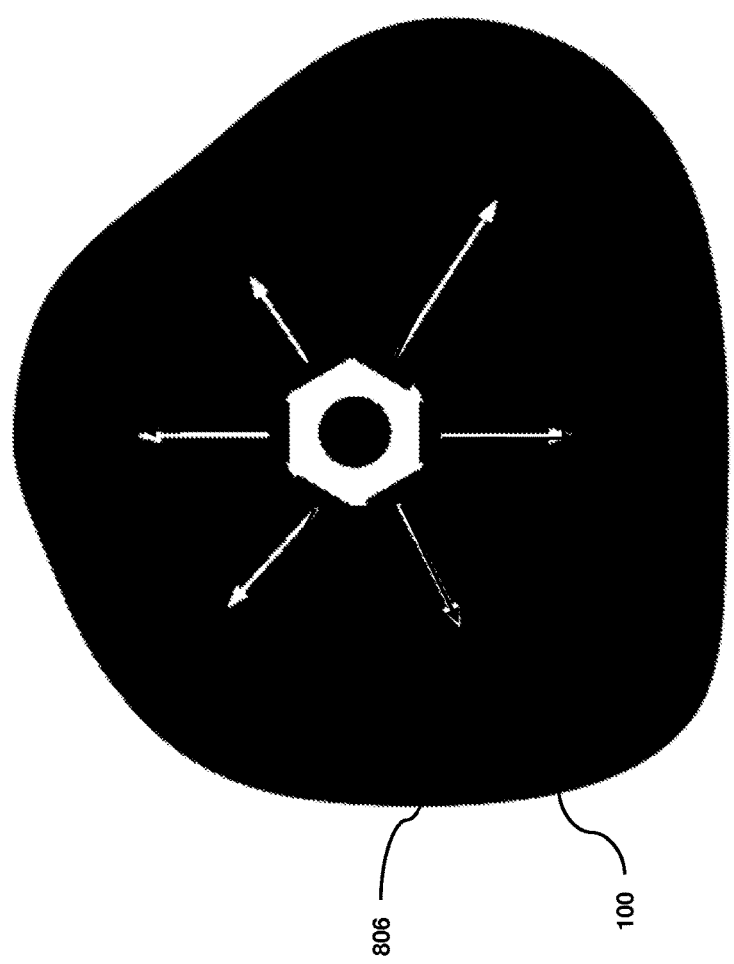
FIG. 8 is a diagrammatic, schematic view of a distal portion of a reduced transducer intravascular device disposed within a human vessel, according to an embodiment of the present disclosure.

FIG. 8 illustrates a diagrammatic, schematic view of a distal portion of a reduced transducer intravascular device 800 disposed within the human vessel 100, according to an embodiment of the present disclosure. The intravascular device 800 can be similar to the intravascular device 102 (FIG. 1) and/or the catheter 600 (FIGS. 6 and 7). In that regard, the intravascular device 800 can include the sensor assembly 110 (FIG. 1), the sensor assembly 400 (FIG. 4), the transducer array 132 (FIG. 1), the transducer array 416 (FIG. 4), and/or the transducer array 602 (FIG. 7). The arrows extending from the intravascular device 800 are representative of the ultrasound emissions from the transducer elements 802.

The intravascular device 800 can be utilized to generate intravascular measurements, such a cross-sectional area and/or a diameter of the vessel 100. The vessel 100 can include a stenosis 806 that is generally representative of any blockage or other structural arrangement that results in a restriction to the flow of fluid through the lumen 120 of the vessel 100. The stenosis 806 decreases the available space for fluid to flow through the lumen 120. In particular, the diameter and/or the cross-sectional area of the lumen 120 are decreased by the stenosis 806. The stenosis 806 can longitudinally extend between a proximal shoulder and a distal shoulder, which are locations in the vessel 100 where the plaque buildup begins/ends. Note that the stenosis 806 is exemplary in nature and should be considered limiting in any way. In that regard, it is understood that the stenosis 806 has other shapes and/or compositions that limit the flow of fluid through the lumen 120 in other instances. While the vessel 100 is illustrated in FIG. 8 as having a single stenosis 806, it is nevertheless understood that the devices, systems, and methods described herein have similar application for a vessel having multiple stenosis regions.

Treatment of the stenosis 806 can include the positioning of a stent within the lumen 120. The stent can be configured to reestablish a normal or near-normal flow of fluid through the lumen 120 by increasing the size or cross-sectional area of the lumen 120. That is, the stent can increase the diameter of the lumen 120 at the narrowest point. A diameter of the stent can be approximately equal to the diameter at the proximal shoulder and/or distal shoulder. The stent can extend between the proximal shoulder and the distal shoulder. The proximal and distal ends of the stent can include stent struts. An efficacious stenting procedure includes properly positioning the stent within the lumen 120, such as when the struts are well apposed to the lumen wall 128.

Embodiments of the present disclosure are suitable for use in a wide variety of vascular applications, including without limitation coronary, peripheral (including but not limited to lower limb, carotid, and neurovascular), renal, and/or venous. Where the vessel 100 is a blood vessel, the stenosis 806 may be a result of plaque buildup, including without limitation plaque components such as fibrous, fibro-lipidic (fibro fatty), necrotic core, calcified (dense calcium), blood, fresh thrombus, and mature thrombus. Generally, the composition of the stenosis will depend on the type of vessel being evaluated. In that regard, it is understood that the concepts of the present disclosure are applicable to virtually any type of blockage or other narrowing of a vessel that results in decreased fluid flow. Some portions of the vessel 100 can have a substantially constant cylindrical profile and some portions of the vessel 100 a non-symmetric and/or otherwise irregular profile. In some instances, the non-symmetric and/or otherwise irregular profile is caused by the stenosis 806, a plaque buildup profile, and/or other irregularities. Thus, it understood references herein to diameter and cross-sectional area are representative of relative dimensions of the lumen 120 and do not imply a circular cross-sectional profile.

In some instances, the intravascular device 800 is configured to collect IVUS data for measurement and/or imaging within the vessel 100 while the intravascular device 800 is stationary. In some embodiments, the intravascular device 800 is configured to collect IVUS data while being moved through the lumen 120. In some instances, the intravascular device 800 is configured to be moved through the lumen 120 and longitudinally across the stenosis 806. Thus, IVUS data can be collected at a plurality of locations of the vessel 100. For example, first and second locations within the vessel 100 can include locations distal to and/or proximal to the stenosis 806. For example, the intravascular device 800 is positioned distal of the stenosis 806 and moved proximally (i.e., pulled back) across the stenosis to a location proximal of the stenosis in some instances. In other instances, the intravascular device 800 is positioned proximal of the stenosis 108 and moved distally across the stenosis to a position distal of the stenosis. Movement of the IVUS device 800, either proximally or distally, is controlled manually by medical personnel (e.g., hand of a surgeon) in some embodiments. In other embodiments, movement of the IVUS device 800, either proximally or distally, is controlled automatically by a movement control device (e.g., a pullback device, such as the Trak Back® II Device available from Volcano Corporation). In that regard, the movement control device controls the movement of the intravascular device 800 at a selectable and known speed (e.g., 2.0 mm/s, 1.0 mm/s, 0.5 mm/s, 0.2 mm/s, etc.) in some instances. Movement of the IVUS device 800 through the vessel is continuous for each pullback or push through, in some instances. In other instances, the intravascular device 800 is moved step-wise through the vessel (i.e., repeatedly moved a fixed amount of distance and/or a fixed amount of time).

Figure 9:
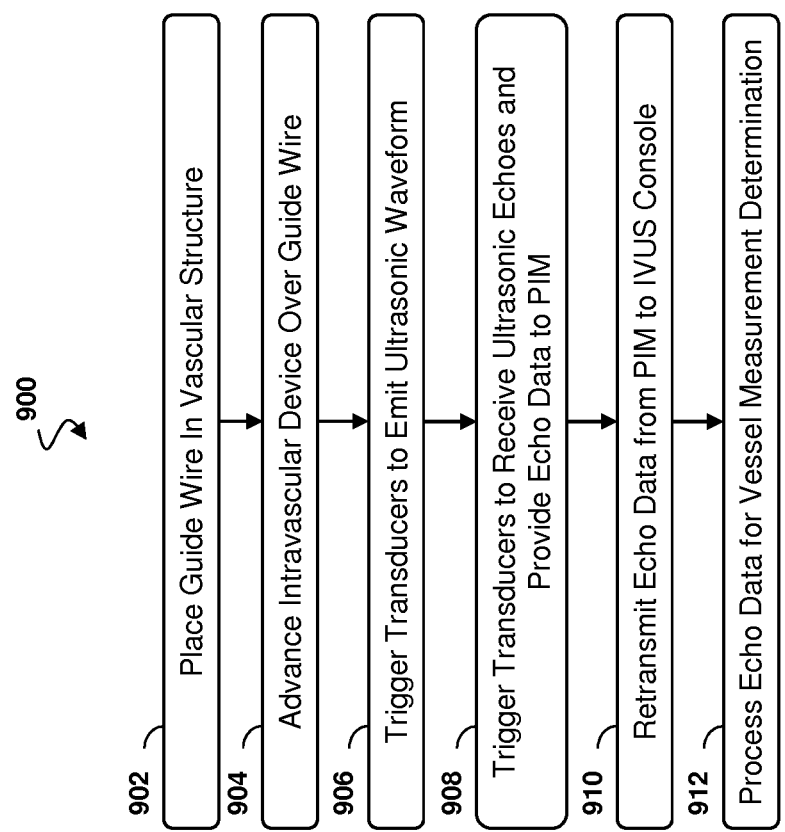
FIG. 9 is a flow diagram illustrating operation of a reduced transducer intravascular device, according to an embodiment of the present disclosure.

FIG. 9 illustrates a flow diagram of method 900 of operating of a reduced transducer intravascular device, according to an embodiment of the present disclosure. For example, the method 900 can be described as a method of generating one or more intravascular measurements. It is understood that additional steps can be provided before, during, and after the steps of method 900, and some of the steps described can be replaced or eliminated for other embodiments of the method. The method 900 can be carried out using any embodiment of the reduced transducer intravascular devices described herein. Thus, while the method 900 is described below in the context of the imaging system 100 of FIG. 1, it is understood that the method 900 can be carried with the scanner assembly 400 (FIGS. 4 and 5), the catheter 600 (FIGS. 6 and 7), and/or the intravascular device 800 (FIG. 8).

Referring to block 902, the method 900 includes a surgeon placing a guidewire in a vascular structure. For example, the guidewire 118 is placed in the vessel 100 (FIG. 1). The guidewire 118 can be threaded through at least a portion of the distal end of the intravascular device 102 before, during, or after placement of the guidewire 118. Referring to block 904 of FIG. 9, the method 900 includes, once the guidewire 118 is in place, advancing the intravascular device 102 over the guidewire 118. Referring to block 906, the method 900 includes activating the scanner assembly 110. Signals sent from the PIM 104 to the scanner assembly 110 via the cable 112 cause transducers within the assembly 110 to emit a specified ultrasonic waveform. The ultrasonic waveform is reflected by one or more structures within the vessel 100. Referring to block 908 of FIG. 9, the method 900 includes receiving the reflections at the transducers within the scanner assembly 110. The received echo data can be amplified for transmission via the cable 112. The echo data is placed on the cable 112 and sent to the PIM 104. The PIM 104 amplifies the echo data and/or performs preliminary pre-processing, in some instances. Referring to block 910 of FIG. 9, the PIM 104 retransmits the echo data to the computing device 106. Referring to block 912 of FIG. 9, the computing device 106 aggregates and assembles the received echo data to determine a measurement of the vessel 100 for display on the monitor 108. The intravascular measurement(s) can include a diameter and/or a cross-sectional area of the lumen 120 of the vessel 100. The computing device 106 can generate display data representative of the intravascular measurement(s) and output the intravascular measurement(s) to the monitor 108.

In some embodiments, the transducer array 132 and/or the intravascular device 102 are oriented at a first angular relation with respect to the vessel 100 when the transducers emit the ultrasound waveforms (block 906) and receive the ultrasonic echoes (block 910). The angular relation can describe a rotation of the transducer array and/or the intravascular device about the longitudinal axis of the vessel (e.g., rotation of the intravascular device 800 of FIG. 8 in the plane of the page). Referring again to FIGS. 1 and 9, the first angular relation can be defined relative to the vessel 100, a fixed point on the intravascular device 102 (such as the guidewire exit port 116), etc. In some embodiments, the method 900 includes reorienting the intravascular device 102 such that the transducer array 132 is oriented at a second angular relation with respect to the vessel 100. For example, the surgeon can manually cause rotation of the intravascular device 102. The method 900 can also include controlling the transducer array 132 to transmit ultrasonic energy and receive ultrasound echoes while the transducer array 132 is oriented at the second angular relation with respect to the vessel 100. In some embodiments, the method 900 includes processing the ultrasound echoes associated with first and second angular relations to generate an average intravascular measurement. For example, the ultrasound echoes associated with two or more angular relations can be processed by the computing device 106 to generate an average diameter and/or cross-sectional area. In some embodiments, the first and second angular relations are the same. For example, the intravascular device 102 is either not reoriented or the intravascular device 102 is reoriented and the transducer array 132 returns to the same angular relation with respect to the vessel 100. When the first and second angular relations are the same, a higher precision intravascular measurement can be generated because the same longitudinal position within the vessel 100 is interrogated with ultrasonic energy while the transducer array 132 is oriented in the same way. In some embodiments, the first and second angular relations are different. In such embodiments, a higher precision intravascular measurement can be generated because irregularities in the shape of the vessel wall 128 can be taken into consideration as the same longitudinal position within the vessel 100 is interrogated with ultrasonic energy while the transducer array 132 is oriented in different ways. In some embodiments, the method 900 includes monitoring the orientation of the transducer array 132. For example, the intravascular device 102 can include a mechanical, electronic, and/or electro-mechanical component, such as on the controller 126, for monitoring rotation.

In some embodiments, the method 900 can include measuring a pressure of blood flow at a first location within the vessel 100. The pressure is measured using the pressure sensor 128 that is disposed at or adjacent the distal portion of the catheter body. In some embodiments, the first location is distal to a stenosis in the vessel 100. In some embodiments, the method 900 includes measuring the pressure of blood flow at a second location within the vessel using the pressure sensor. In some embodiments, the second location is proximal to the stenosis in the vessel 100. The pressure measurement(s) can be output to the display 108. In some embodiments, the method 900 includes computing a fractional flow reserve (FFR) using the pressure measurements at the first and second locations. The FFR can be output to the display 108.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An intravascular ultrasound (IVUS) device, comprising:
a catheter body configured to be positioned within a blood vessel of a patient, the catheter body comprising a proximal portion, an opposing distal portion, and a ferrule defining a guidewire-through lumen extending through at least the distal portion of the catheter body; and
a transducer array disposed adjacent the distal portion, wherein the transducer array is rotationally and longitudinally fixed relative to the ferrule, the transducer array having a plurality of transducers and each of the plurality of transducers having a transducer width along a direction perpendicular to a longitudinal direction of the catheter body, wherein the plurality of transducers are spaced apart from one another by at least a spacing circumferentially around the catheter body, the spacing being at least twice as large as the transducer width,
wherein the guidewire-through lumen extends through the transducer array.

2. The device of claim 1, wherein the transducer array has less than 24 transducers.

3. The device of claim 2, wherein the transducer array has less than 12 transducers.

4. The device of claim 3, wherein the transducer array has 6 transducers.

5. The device of claim 1, wherein the spacing is greater than 4 times the transducer width.

6. The device of claim 1, wherein the spacing is greater than 8 times the transducer width.

7. The device of claim 1, wherein the transducer array is connected to a control circuit, the control circuit having a width greater than the transducer width and equal to or greater than the spacing.

8. The device of claim 7, further comprising comprise a flexible substrate, wherein the transducer array and the control circuit are coupled to the flexible substrate.

9. The device of claim 1, further including a pressure sensor disposed adjacent the transducer array.

10. The device of claim 9, further including a control circuit receiving signals from both the transducer array and the pressure sensor.

11. A minimally invasive measuring device, comprising:
an elongate body configured for insertion into a body lumen of a patient, the elongate body comprising:
a proximal portion;
an opposing distal portion; and
a ferrule defining a guidewire-through lumen extending through at least the distal portion of the elongate body; and
a transducer array disposed adjacent the distal portion, wherein the transducer array is rotationally and longitudinally fixed relative to the ferrule, the transducer array having a plurality of transducers each having a width along a direction perpendicular to a longitudinal direction of the elongate body, the plurality of transducers spaced apart from one another circumferentially around the elongate body by a spacing that is at least twice as large as the width, the plurality of transducers comprising 3 to 16 transducers,
wherein the guidewire-through lumen extends through the transducer array.

12. The device of claim 11, wherein the plurality of transducers are equally spaced about the circumference of the elongate body.

13. The device of claim 11, further including a single control circuit disposed adjacent the distal portion for controlling the transducer array.

14. The device of claim 13, further including a pressure sensor disposed adjacent the distal portion and in communication with the single control circuit.

15. The device of claim 14, wherein the transducer array is positioned more distally than the pressure sensor.

16. The device of claim 13, wherein the single control circuit comprises a single application specific integrated circuit (ASIC).

17. The device of claim 11, wherein the guidewire-through lumen terminates prior to reaching the proximal portion.

18. The device of claim 11, further comprising:
a single application specific integrated circuit (ASIC) in communication with the transducer array; and
a flexible substrate positioned around the ferrule, wherein the flexible substrate comprises a proximal portion and a distal portion, wherein the single ASIC is coupled to the flexible substrate at the proximal portion and the transducer array is coupled to the flexible substrate at the distal portion.

* * * * *